United States Patent
Utsugida et al.

(10) Patent No.: US 10,850,019 B2
(45) Date of Patent: *Dec. 1, 2020

(54) CIRCULATION APPARATUS AND METHOD FOR CONTROLLING THE SAME

(71) Applicant: TERUMO KABUSHIKI KAISHA, Tokyo (JP)

(72) Inventors: Tomoki Utsugida, Kanagawa (JP); Yosuke Itamochi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 388 days.

This patent is subject to a terminal disclaimer.

(21) Appl. No.: 15/938,447

(22) Filed: Mar. 28, 2018

(65) Prior Publication Data

US 2018/0214624 A1    Aug. 2, 2018

Related U.S. Application Data

(63) Continuation of application No. 14/868,467, filed on Sep. 29, 2015, now Pat. No. 9,968,724, which is a
(Continued)

(51) Int. Cl.
*A61M 1/16* (2006.01)
*A61M 1/36* (2006.01)

(52) U.S. Cl.
CPC ........ *A61M 1/1698* (2013.01); *A61M 1/3666* (2013.01); *A61M 1/3667* (2014.02);
(Continued)

(58) Field of Classification Search
CPC .............. A61M 1/1698; A61M 1/3666; A61M 1/3667; A61M 2202/0208;
(Continued)

(56) References Cited

U.S. PATENT DOCUMENTS

| 4,493,692 A | 1/1985 | Reed |
| 5,695,717 A | 12/1997 | Polaschegg et al. |

(Continued)

FOREIGN PATENT DOCUMENTS

| JP | 62-82969 A | 4/1987 |
| JP | 07-136251 A | 5/1995 |

(Continued)

OTHER PUBLICATIONS

International Search Report (PCT/ISA/210) dated May 7, 2013, by the Japanese Patent Office as the International Searching Authority for International Application No. PCT/JP2013/002231.
(Continued)

*Primary Examiner* — Benjamin J Klein
(74) *Attorney, Agent, or Firm* — Buchanan Ingersoll & Rooney PC

(57) ABSTRACT

An artificial lung in a circulation apparatus can be monitored and be maintained in a safe condition without manual assistance. As an extracorporeal circulation mode starts, it is determined first whether or not gas exchange of the artificial lung is carried out within a normal range, based on oxygen concentration which is detected by an oxygen sensor positioned at a downstream place in the artificial lung. If the gas exchange is carried out within the normal range, an estimated value for gas supply volume of a gas blender is maintained. When oxygen concentration exceeding the normal range is detected, the gas blender is controlled so as to revise the gas supply volume downward. In addition, when oxygen concentration falls below the normal range, the gas blender is controlled so as to revise the gas supply volume upward.

6 Claims, 5 Drawing Sheets

Related U.S. Application Data continuation of application No. PCT/JP2013/002231, filed on Apr. 1, 2013.

(52) U.S. Cl.
CPC . *A61M 2202/0208* (2013.01); *A61M 2205/18* (2013.01); *A61M 2205/3327* (2013.01); *A61M 2205/3334* (2013.01); *A61M 2205/7554* (2013.01)

(58) Field of Classification Search
CPC ...... A61M 2205/18; A61M 2205/3327; A61M 2205/3334; A61M 2205/7554
See application file for complete search history.

(56) References Cited

U.S. PATENT DOCUMENTS

| | | | |
|---|---|---|---|
| 5,810,759 A | 9/1998 | Merz | |
| 9,968,724 B2 * | 5/2018 | Utsugida | A61M 1/3666 |
| 2007/0276508 A1 | 11/2007 | Fischer et al. | |
| 2009/0081079 A1 | 3/2009 | Johns | |
| 2010/0101657 A1 | 4/2010 | Morley | |

FOREIGN PATENT DOCUMENTS

| | | |
|---|---|---|
| JP | 8-182758 A | 7/1996 |
| JP | 2000-271213 | 10/2000 |
| JP | 2007-289695 A | 11/2007 |
| JP | 2009-533122 A | 9/2009 |
| WO | WO 2012/013925 A2 | 2/2012 |

OTHER PUBLICATIONS

Extended European Search Report dated Oct. 27, 2016, by the European Patent Office in corresponding European Application No. 13880743.3-1651. (7 pages).

Office Action (Decision to Grant a Patent) dated Jun. 2, 2017, by the Japanese Patent Office in corresponding Japanese Patent Application No. 2016-171289, and an English translation of the Office Action. (6 pages).

Office Action (Notification of Reasons for Refusal) dated May 19, 2016, by the Japanese Patent Office in corresponding Japanese Patent Application No. 2015-509579, and an English translation of the Office Action. (7 pages).

Japanese Journal of Extra-Corporeal Technology vol. 27, No. 2, pp. 13-15, 2000.

Office Action (Invitation pursuant to Article 94(3) and Rule 71(1) EPC (5 pages).

\* cited by examiner

CIRCULATION APPARATUS AND METHOD FOR CONTROLLING THE SAME

CROSS-REFERENCES TO RELATED APPLICATIONS

This application is a continuation of U.S. application Ser. No. 14/868,467 filed on Sep. 29, 2015, which is a continuation of International Application No. PCT/JP2013/002231 filed on Apr. 1, 2013, the entire content of each of which is incorporated herein by reference.

TECHNICAL FIELD

The present invention relates to a circulation apparatus and a method of controlling the same.

BACKGROUND DISCUSSION

An artificial lung, such as disclosed in JP-A-2007-289695, is configured to be used with an extracorporeal circulation apparatus to cause the blood to take in oxygen and eliminate carbon dioxide gas while in contact with air. The artificial lung has a structure in which a gas exchange membrane is interposed between the blood and air so that they are not in direct contact with each other.

SUMMARY

When an extracorporeal circulation apparatus is in operation, the efficiency of gas exchange of the artificial lung, and thus the resultant blood oxygen concentration, can fluctuate. Internal factors such as a material, a structure, and the like of a gas exchange membrane, and external factors such as a temperature, humidity, and the like, can affect the efficiency of exchange. Particularly, the gas exchange membrane sometimes has a structure in which a number of minute holes are arranged side by side. Thus, high humidity can cause deterioration of the efficiency of exchange. Therefore, a signal of a sensor detecting blood oxygen concentration (e.g., through a display screen which is provided on the circulation apparatus) is generally monitored and, as necessary, supply capacity of a gas blender apparatus which is connected to the artificial lung is manually adjusted. The gas blender apparatuses generally supply mixed gas of 100% oxygen and compressed air, and in order to adjust the supply volume, opening and closing of a valve (i.e., an opening ratio or a valve open ratio) are manually adjusted. In other words, as blood oxygen concentration falls, the opening ratio of the valve in the gas blender apparatus is raised, thereby increasing the supply volume of gas (oxygen concentration) per unit time. In addition, when blood oxygen concentration reaches a certain degree or higher, the opening ratio of the valve in the gas blender apparatus is lowered so as to perform an operation of reducing the supply volume of gas.

The above-described operation can be performed within a relatively short time interval. However, a problematic phenomenon can occur in which a blood plasma liquid is exudated as droplets on a surface of the gas exchange membrane on a side where gas passes through, as time elapses. This phenomenon is referred to as the "blood plasma leak". If left uncorrected, most of the gas exchange membrane will occur in a state of being covered with the blood plasma liquid. In such a state, most of gas exchange holes are blocked by the blood plasma liquid, extremely deteriorating the efficiency of exchange. Due to the potential of such problems, normally, at an interval of three hours to six hours, for approximately three minutes per session, the opening ratio of the valve in the gas blender apparatus is raised (or the valve fully opened) so as to perform an operation of blowing off the blood plasma liquid on the gas exchange membrane by causing strong gas to pass through the gas exchange membrane. This operation is referred to as the flush operation. In addition, even when there is no fluctuation in blood oxygen concentration for a long period of time, there can occur a phenomenon of dew condensation due to moisture in the air which enters the low-temperature artificial lung. This phenomenon is referred to as the "wet lung" and can also result in deteriorated function of the apparatus, and so it is also desirable, in order to eliminate moisture by dew condensation, to flush the gas every several hours or at a fixed interval.

However, since the flush operation is manually performed at an empirical time interval as described above, it may not be possible to completely avoid an occurrence of an accident caused by neglecting the flush operation. In addition, conversely, if the flush operation is performed more than necessary, there can be other problems, such as an unnecessary increase in consumption rate of a gas cylinder.

In taking the above-described circumstances into consideration, there is provided a technology in which the artificial lung in the circulation apparatus can be monitored and be maintained in a safe condition without manual assistance.

In order to achieve the above-described and other objectives, a circulation apparatus includes a constitution as described below. That is, a circulation apparatus which causes blood of a patient to circulate outside a human body by using a circulation circuit, the apparatus including: detection means for detecting blood oxygen concentration after gas exchange performed in an artificial lung while being positioned on a downstream side of the artificial lung which is installed on the circulation circuit; determination means for determining whether blood oxygen concentration detected by the detection means is within a target range set in advance, exceeds the target range, or falls below the target range; gas supply means for supplying gas including at least oxygen to the artificial lung while having changeable supply volume per unit time; and control means for controlling gas supply volume of the gas supply means in accordance with a determination result of the determination means.

Accordingly, the artificial lung in the circulation apparatus can be monitored and be maintained in a safe condition without manual assistance.

Other characteristics and advantages will be clearly described with reference to the accompanying drawings. In the accompanying drawings, the same or similar constitutions will be applied with the same reference numerals and signs.

BRIEF DESCRIPTION OF THE DRAWINGS

The accompanying drawings illustrate exemplary embodiments of the present disclosure.

DETAILED DESCRIPTION

Hereinafter, embodiments of the present disclosure will be described in detail with reference to the accompanying drawings.

First Embodiment

<1. Overall Constitution of Extracorporeal Circulation Apparatus>

Figure 1:
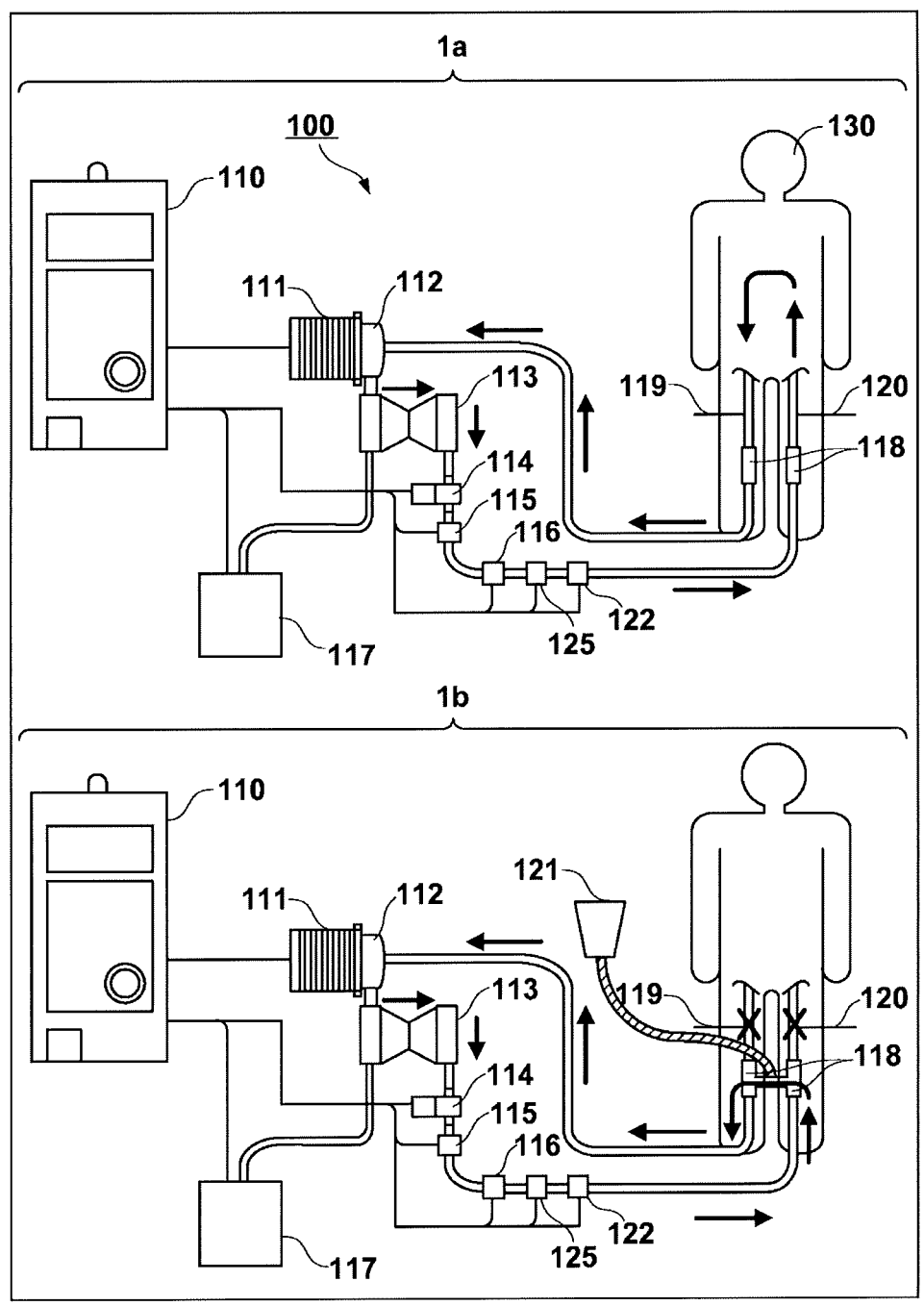
FIG. 1 is a diagram illustrating an overall constitution of an extracorporeal circulation apparatus in an embodiment.

First, an overall constitution of an extracorporeal circulation apparatus according to an embodiment will be described. FIG. 1 illustrates an example of an overall constitution of an extracorporeal circulation apparatus 100 in a circulation state 1a and a priming state 1b in the embodiment.

The extracorporeal circulation apparatus 100 is used not only in extracorporeal circulation during cardiac surgery and the like but also in auxiliary circulation techniques such as PCPS, ECMO, and the like, thereby performing a cardiopulmonary support operation (an extracorporeal circulation operation and a priming operation). The extracorporeal circulation apparatus 100 includes a blood extracorporeal circulation circuit (hereinafter, referred to as the circulation circuit) indicated by arrows in the diagram. In the extracorporeal circulation apparatus 100, after the priming operation is performed, blood of a patient 130 is subjected to extracorporeal circulation by using the circulation circuit.

The priming operation denotes an operation in which a priming liquid circulates inside the circulation circuit so as to eliminate air bubbles inside the circuit in a state where the circulation circuit is sufficiently filled with the priming liquid (for example, a physiological salt solution).

The extracorporeal circulation apparatus 100 includes a controller 110 which functions as a control device, a drive motor 111, a centrifugal pump 112, an artificial lung 113, a gas blender 117 which is an oxygen supply source, a cannula (vein side) 119, a cannula (artery side) 120, an air bubble sensor 114, a flow rate sensor 115, a blood filter 116, branch lines 118, a clamp 122, and a blood oxygen concentration sensor 125. Each of the constitutions is connected to one another through flexible tubes and the like, and each lumen of the tubes constitutes a flow path of blood or the priming liquid.

The cannula (artery side) 120 performs blood transmission into the body of the patient 130, and the cannula (vein side) 119 performs blood extraction from the inside of the body of the patient 130.

The centrifugal pump 112 (also referred to as the centrifugal artificial heart) drives a rotary body provided therein so as to apply pressure to blood, thereby causing the blood to circulate inside the circulation circuit. The drive motor 111 applies a rotary drive force to the rotary body of the centrifugal pump 112. However, the pump is not limited to the centrifugal pump, and a roller pump or the like may be adopted.

The artificial lung 113 performs circulation of blood and gas exchange (oxygenation, carbon dioxide elimination, and the like) of blood (will be described later in detail). The gas blender 117 is connected to an oxygen cylinder and an air cylinder, and supplies mixed gas thereof to the artificial lung 113. The gas blender 117 has a structure in which volume of gas (hereinafter, the gas supply volume) per unit time supplied to the artificial lung 113 can be adjusted in accordance with a control signal from the controller 110. Therefore, the gas blender 117 of the embodiment has a drive system and a circuit for adjusting a valve open ratio (an opening ratio) of a valve (not illustrated) in accordance with a signal from the controller 110. The valve open ratio of the valve inside the gas blender 117 of the embodiment is adjustable in five levels represented by Vmin, V−, V0, V+, and Vmax, and detailed descriptions thereof will be given later. The level Vmin denotes a fully closed state and also denotes a state before functioning as the circulation circuit. The level V0 represents the valve open ratio when blood oxygen concentration is in a normal range. The level V− is a level to reduce the supply volume as much as ΔV than the level V0 and is applied when blood oxygen concentration exceeds the normal range. The level V+ is a level to increase the supply volume as much as ΔV than the level V0 and is applied when blood oxygen concentration falls below the normal range. The level Vmax represents the valve open ratio at the time of flush processing and represents the valve open ratio for forcefully supplying gas sufficient to blow off a blood plasma liquid which is exudated on a gas exchange membrane in the artificial lung 113. Typically, the valve is in a fully open state at the level Vmax. However, it is acceptable as long as power to blow off the blood plasma liquid can be obtained, and thus, the valve is not necessarily fully open.

The air bubble sensor 114 detects air bubbles which are included in the priming liquid or blood flowing inside the circulation circuit at the time of the priming operation and the extracorporeal circulation operation by a predetermined detection method (ultrasound, light, or the like). The blood filter 116 filters blood and eliminates air bubbles in blood. The flow rate sensor 115 is constituted to have a built-in ultrasound transceiver, for example, and detects a flow rate of the priming liquid or blood inside the circulation circuit. A blood oxygen concentration sensor 125 is positioned at a downstream place in the artificial lung 113 and detects oxygen concentration in blood (to be accurate, oxygen saturation SpO2 in oxidized blood).

The clamp 122 is a member which blocks the tubes so as to forcedly stop blood transmission into the body of the patient 130 at the time of the extracorporeal circulation operation. The clamp 122 can automatically perform a blocking operation in an interlocking manner when an occurrence of abnormality requiring an immediate stop of blood transmission is determined based on an output signal from the air bubble sensor 114.

The branch lines 118 switch the flow path of the circulation circuit. Specifically, at the time of the extracorporeal circulation operation in which blood of the patient 130 is subjected to extracorporeal circulation, as illustrated in circulation state 1a of FIG. 1, the circulation circuit passing through the inside of the body of the patient 130 is established, thereby causing blood to circulate outside the body of the patient 130. At the time of the priming operation, as illustrated in priming state 1b of FIG. 1, the path of the circulation circuit into the body of the patient 130 is shut off by the branch lines 118 so as to establish the circulation circuit passing through only the outside of the body of the patient 130 (in other words, the circulation circuit not passing through the inside of the patient 130) and the inside of the circulation circuit is filled with the priming liquid, thereby causing the priming liquid to circulate therein (without passing through the inside of the patient). One or a plurality of air bubble discharge ports (not illustrated) for discharging air bubbles are provided on the circulation circuit. As the priming liquid circulates inside the circulation circuit for a plurality of laps, air bubbles inside the circulation circuit are discharged through the air bubble discharge port.

The controller 110 performs integrated controlling of the extracorporeal circulation operation and the priming operation of the extracorporeal circulation apparatus 100. For example, the controller 110 controls the drive motor 111 so as to drive the centrifugal pump 112. In addition, the controller 110 controls the air bubble sensor 114 to obtain an output signal from the air bubble sensor 114 or controls the flow rate sensor 115 to obtain a flow rate value. Moreover, in an extracorporeal circulation operation mode, when abnormality requiring a stop of blood transmission is detected based on the output signal from the air bubble sensor 114, the clamp 122 is in a blocking operation. Furthermore, the controller 110 also performs processing of adjusting the gas supply volume of the gas blender 117 in accordance with oxygen concentration which is detected by a blood oxygen concentration sensor.

Subsequently, descriptions will be given regarding a flow of processing when performing the cardiopulmonary support operation (the extracorporeal circulation operation and the priming operation) by using the extracorporeal circulation apparatus 100 illustrated in FIG. 1.

As the cardiopulmonary support operation starts, the controller 110 controls execution of the priming operation. At the time of the priming operation, as illustrated in priming state 1b of FIG. 1, the circulation circuit not passing through the inside of the body of the patient 130 is established by the branch lines 118. In addition, in this case, a priming liquid supply source 121 is connected to the branch lines 118, and the priming liquid is supplied to the inside of the circulation circuit from the priming liquid supply source 121. In this manner, the inside of the circulation circuit is filled with the priming liquid.

Then, the centrifugal pump 112 is controlled to be driven by the controller 110, and the priming liquid circulates inside the circulation circuit for the plurality of laps. As a result of the circulation, air bubbles inside the circulation circuit are discharged through the air bubble discharge port and the like. In addition, the presence or absence of air bubbles flowing inside the circulation circuit may be detected by the air bubble sensor 114 at the time of the priming operation.

A user who has confirmed completion of priming stops driving of the centrifugal pump and switches the branch lines 118, thereby establishing the circulation circuit passing through the inside of the body of the patient 130 as illustrated in circulation state 1a of FIG. 1. Thereafter, the user operates the controller 110 so as to set a target flow rate and inputs an instruction to start extracorporeal circulation. As a result, as the controller 110 drives the pump 112 based on the set information, blood of the patient 130 is in extracorporeal circulation. In addition, the controller 110 sets the gas supply volume of the gas blender 117 to the level V0 as the initial value so as to start supplying gas.

As the extracorporeal circulation operation starts, blood subjected to blood extraction through the cannula (vein side) 119 flows into the artificial lung 113 via the centrifugal pump 112. As described above, the artificial lung 113 performs gas exchange, that is, gas exchange processing such as oxygenation, carbon dioxide elimination, and the like in response to gas supplied from the gas blender 117, thereby supplying blood after gas exchange to the downstream place. Thereafter, blood which is filtered via the blood filter 116 and the like is subjected to blood transmission into the body of the patient 130 through the cannula (artery side) 120. The flowing of blood of the patient 130 from the cannula (vein side) 119 to the cannula (artery side) 120 is continuously performed. In the extracorporeal circulation operation mode, processing is performed in accordance with signals from the various sensors. For example, when air bubbles inside the circulation circuit are detected by the air bubble sensor 114 and there is a need to stop blood transmission, the blocking operation of the clamp 122 is performed. In addition, in accordance with oxygen concentration detected by a blood oxygen concentration sensor 125, the controller 110 is controlled to adjust the efficiency of gas exchange of the artificial lung 113 (will be described later in detail).

Hereinbefore, descriptions are given regarding the example of the overall constitution of the extracorporeal circulation apparatus 100 and flowing of the cardiopulmonary support operation in the present embodiment. However, the constitutions of the extracorporeal circulation apparatus 100 illustrated in FIG. 1 are merely examples, and thus, the constitutions may be appropriately changed.

<2. Functional Constitution of Controller>

Figure 2:
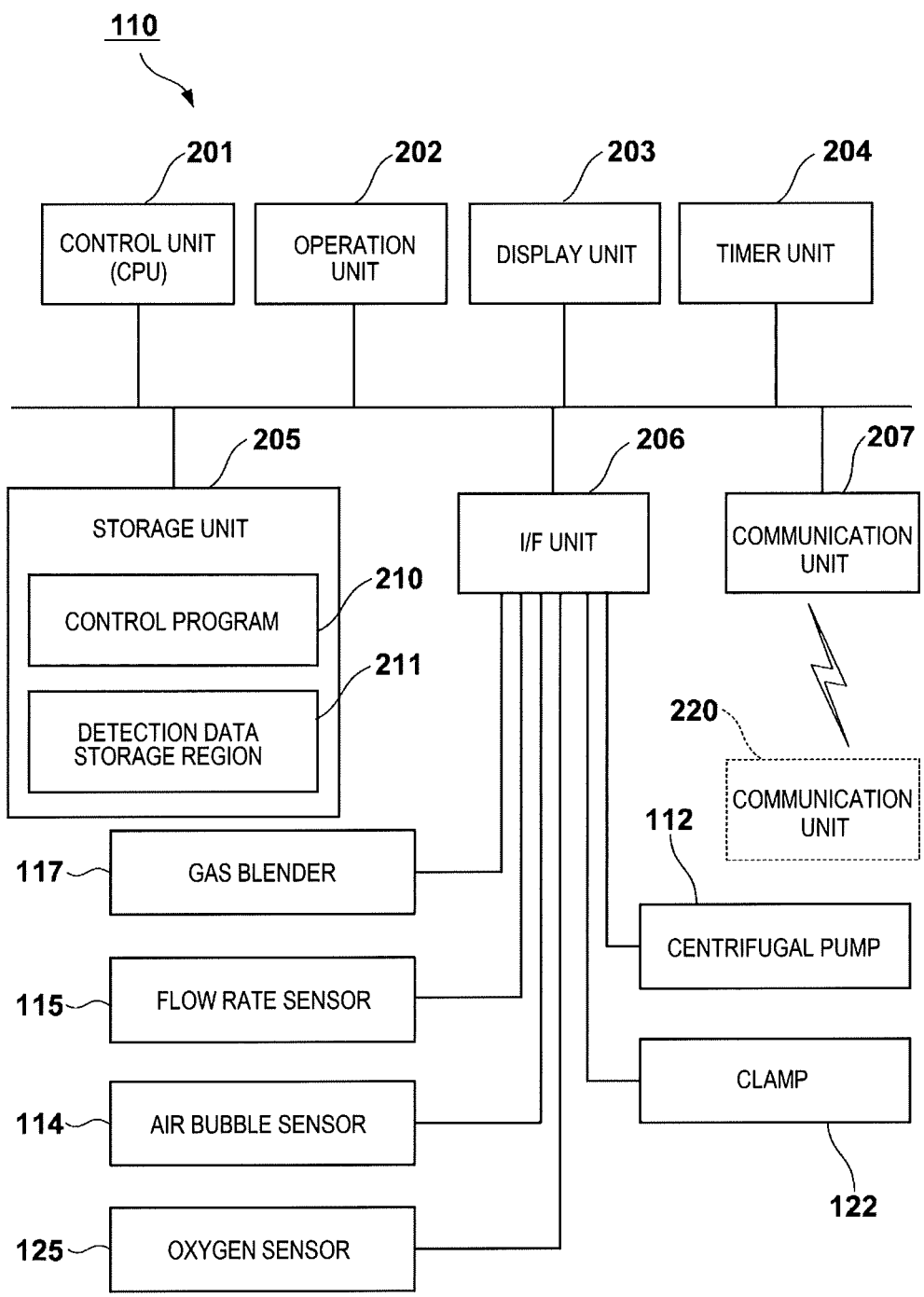
FIG. 2 is a diagram illustrating an example of a functional constitution of a controller of the extracorporeal circulation apparatus.

Subsequently, with reference to FIG. 2, descriptions will be given regarding an example of the functional constitution of the controller 110 illustrated in FIG. 1.

As the functional constitution thereof, the controller 110 includes a control unit 201, an operation unit 202, a display unit 203, a timer unit 204, a storage unit (a recording medium which can be read by a computer) 205, an I/F unit 206, and a communication unit 207.

The control unit 201 constituted of a central processing unit (CPU) controls the controller 110 and also controls the circulation circuit.

For example, the operation unit 202 is realized with various buttons and the like, and a health care worker inputs instruction therethrough. For example, the display unit 203 is realized with a display device such as a monitor and the like (including an output unit which outputs an audio warning) and displays various items of information (including a message) to a user. A portion or the entirety of the operation unit 202 and the display unit 203 may be realized in a touch panel with an audio speaker, for example.

The timer unit 204 performs timekeeping for various time periods. For example, the storage unit 205 is realized with ROM, RAM, and the like and includes a control program 210 for realizing the extracorporeal circulation operation mode in order to perform an operation as the circulation apparatus, and a detection data storage region 211 for storing detection results detected by each sensor. As the control program related to a continuous operation mode is executed, the control unit 201 executes the above-described priming processing and subsequently inputs setting of a target flow rate from the operation unit 202, thereby executing driving control of the pump 112 via the I/F unit 206 or processing of extracorporeal circulation in accordance with the detection results of the various sensors.

The communication unit 207 performs communication with a communication unit 220 with which a health care worker is equipped. Communication between the communication unit 207 and the communication unit 220 may be short-range radio communication such as Bluetooth (registered trademark) and the like, or radio communication through wireless LAN such as Wi-Fi and the like.

Hereinbefore, descriptions are given regarding the example of the functional constitution of the controller 110. The functional constitution illustrated in FIG. 2 is merely an example. Thus, a new constitution may be added, and an unnecessary constitution may be appropriately omitted.

The present embodiment is characterized in processing for favorably maintaining gas exchange of the artificial lung 113 during execution of the extracorporeal circulation operation mode after the priming processing. Therefore, hereinafter, descriptions will be given mainly regarding the extracorporeal circulation operation mode mainly upon the related points.

<3. Overview of Extracorporeal Circulation Operation Mode on Basis of Output Signal from Oxygen Sensor>

In processing of the extracorporeal circulation apparatus, performing of blood circulation at a target flow rate is an important factor. However, the extracorporeal circulation apparatus in the embodiment is characterized in the point of evaluating processing capability of the artificial lung 113 by a blood oxygen concentration sensor 125 and maintaining the efficiency of gas exchange of the artificial lung 113 in a favorable state by controlling the gas blender 117. Therefore, hereinafter, descriptions will be focused on the points thereof.

Figure 3:
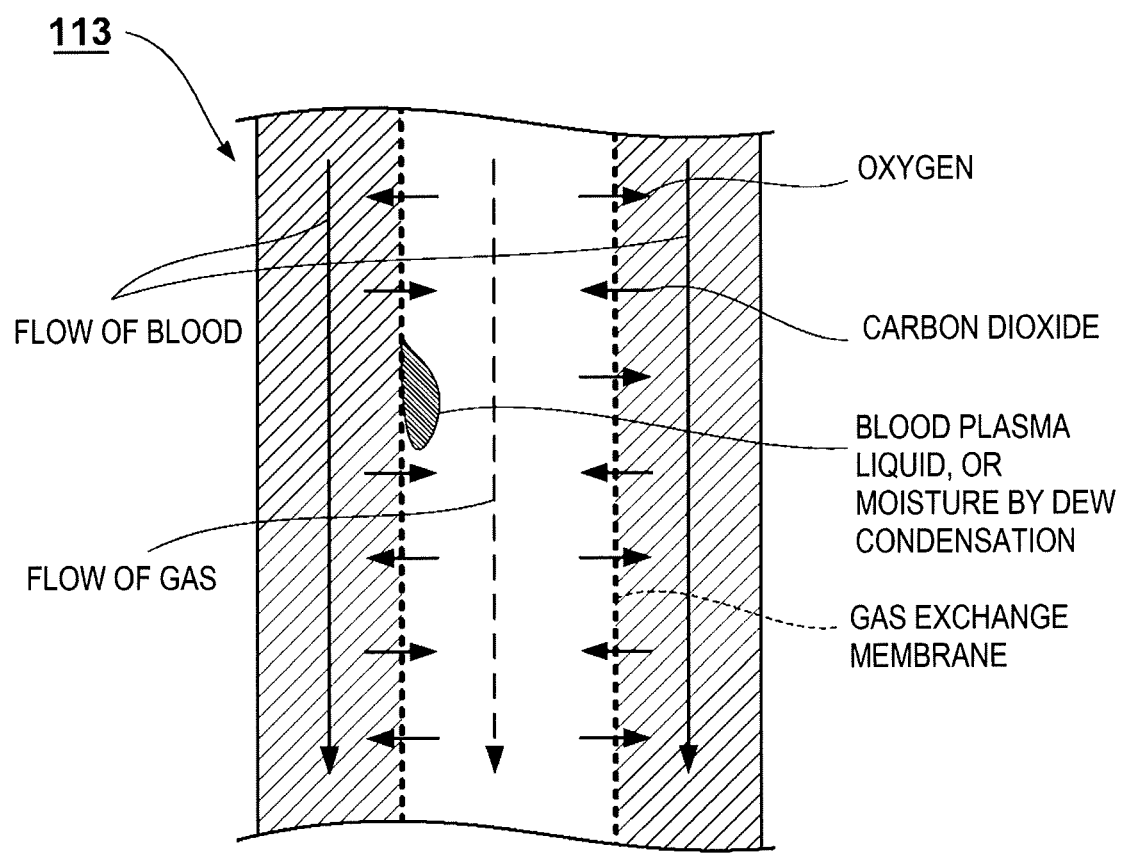
FIG. 3 is a diagram for illustrating a structure of an artificial lung and a principle of gas exchange.

As described above, the artificial lung 113 utilizes properties of blood which takes in oxygen and discharges carbonic acid gas (carbon dioxide) when coming into contact with air. However, blood coagulates when coming into direct contact with air. Therefore, the gas exchange membrane is generally interposed therebetween. FIG. 3 is a conceptual diagram of the artificial lung 113. The artificial lung 113 has the structure in which a portion where blood flows and a portion where gas supplied from the gas blender 117 flows are partitioned by the gas exchange membrane. Through the operation of the gas exchange membrane, oxygen included in a gas supply path is taken in blood and carbon dioxide in blood is discharged to the gas supply path. Normally, the artificial lung 113 is structured to have a plurality of the structures in the diagram in order to enhance the efficiency of gas exchange.

The controller 110 in the embodiment determines whether or not gas exchange is normally performed, based on oxygen concentration detected by a blood oxygen concentration sensor 125 which is positioned at the downstream place in the artificial lung 113. Then, the controller 110 controls the gas blender 117 in accordance with the oxygen concentration, thereby maintaining gas exchange of the artificial lung 113 to be in a normal state.

Specifically, threshold values for determining that gas exchange is normally performed are represented by T1 and T2 (in this case, the relationship therebetween is T1<T2), and oxygen concentration detected by a blood oxygen concentration sensor 125 is defined as D.

When $T1 \leq D \leq T2$, it is determined that the artificial lung 113 normally performs gas exchange, and the controller 110 sets the gas supply volume of the gas blender 117 to the level V0. In addition, when D<T1, oxygen concentration falls below the lower limit of the normal range. Therefore, in order to raise a gas exchange rate, the controller 110 sets the gas supply volume of the gas blender 117 to the level V+ which is increased as much as ΔV. Meanwhile, when D>T2, oxygen concentration exceeds the upper limit of the normal range. Therefore, in order to reduce the gas exchange rate, the controller 110 sets the gas supply volume of the gas blender 117 to the level V− which is decreased as much as ΔV. In all cases, when the oxygen concentration D is within the normal range, the gas blender 117 is set to the level V0 again. In accordance with a signal from the controller, the gas blender 117 drives a drive circuit of the valve (not illustrated), thereby adjusting the valve open ratio of the valve.

A blood oxygen concentration sensor 125 detects oxygen concentration in blood at an interval of approximately 50 ms. However, since a detection result thereof includes a measurement error, there is a little fluctuation in the time axis. In order to prevent the fluctuation, the controller 110 in the embodiment holds ten latest results of oxygen concentration obtained by a blood oxygen concentration sensor 125 and stores the detected oxygen concentration in the detection data storage region 211, thereby calculating an average value thereof as the current oxygen concentration D.

As a result described above, even though the gas exchange rate of the artificial lung 113 fluctuates due to an internal factor or an external factor, it is possible to cause the artificial lung 113 so as to be operated within the normal range. The above-described processing sufficiently covers a case where the circulation circuit is used for a patient in a surgical operation and the operation time is relatively short.

However, as gas exchange is continuously performed by the artificial lung 113, droplets of the blood plasma liquid are gradually formed on the gas exchange membrane as illustrated in FIG. 3. As the gas exchange membrane is in progress being covered with the blood plasma liquid, the gas exchange rate drops naturally. As the gas exchange rate drops, blood oxygen concentration falls as a result thereof. Then, the controller 110 continues to output signals to the gas blender 117 so as to raise the gas supply volume to the level V+ and to supply gas. In spite of that, the blood oxygen concentration D cannot be prevented from falling. It is because the force is insufficient to blow off the blood plasma liquid even though the gas supply volume is set to the level V+. In a case of such a state, it is determined that flush processing needs to be performed. Therefore, in the embodiment, a threshold value T0 which is much lower than the lower limit threshold value T1 for determining the normal range is set. When the blood oxygen concentration D falls below the threshold value T0, the controller 110 determines to execute the flush processing, and the gas supply volume of the gas blender 117 is set to the level Vmax in order to inject gas as much to blow off the blood plasma liquid in the artificial lung 113.

In addition, in the embodiment, the flush processing is performed when the oxygen concentration D is equal to or greater than the threshold value T0 and less than the threshold value T1 and when the time period is equal to or exceeds a time period set in advance. It is because when the oxygen concentration D continues to be equal to or greater than the threshold value T0 and less than T1, it is possible to determine that there is an occurrence of a blood plasma leak to a certain extent in the gas exchange membrane inside the artificial lung 113 as well.

Normally, the time period for manually performing the flush operation per session takes approximately three minutes. Therefore, the level Vmax is continuously set for three minutes in the present embodiment as well. In addition, deterioration of the gas exchange rate due to the blood plasma liquid covering the gas exchange membrane is improved through the flush operation, and the next flush operation is performed after an elapsed time of at least three hours. In addition, the flush operation denotes that the artificial lung is applied with high gas pressure. Thus, a burden is applied to the artificial lung 113, and there is a concern that the product life cycle is shortened. Moreover, as high gas pressure is continuously applied thereto more than necessary, there is a high possibility that air bubbles are generated in blood and the gas tank of the gas blender 117 is instantly consumed.

Therefore, in the present embodiment, similar to the case of the manual operation, the flush operation is not performed again until a predetermined time period (three hours) elapses since the previous flush processing. Conversely, when the blood-oxygen concentration D falls below the threshold value T0 before the predetermined time period elapses since the previous flush processing is executed, it is presumed that there is an occurrence of an abnormal state such as a run-out state of the gas cylinder which is connected to or accommodated in the gas blender 117, gas leakage at somewhere between the gas blender 117 and the artificial lung 113, and the like. In such a case, a warning alarm is issued. The warning alarm may be issued in any type of an audio alarm and a displayed warning message, and may be issued in both thereof.

<4. Flow of Processing of Extracorporeal Circulation Operation Mode>

Figure 4:
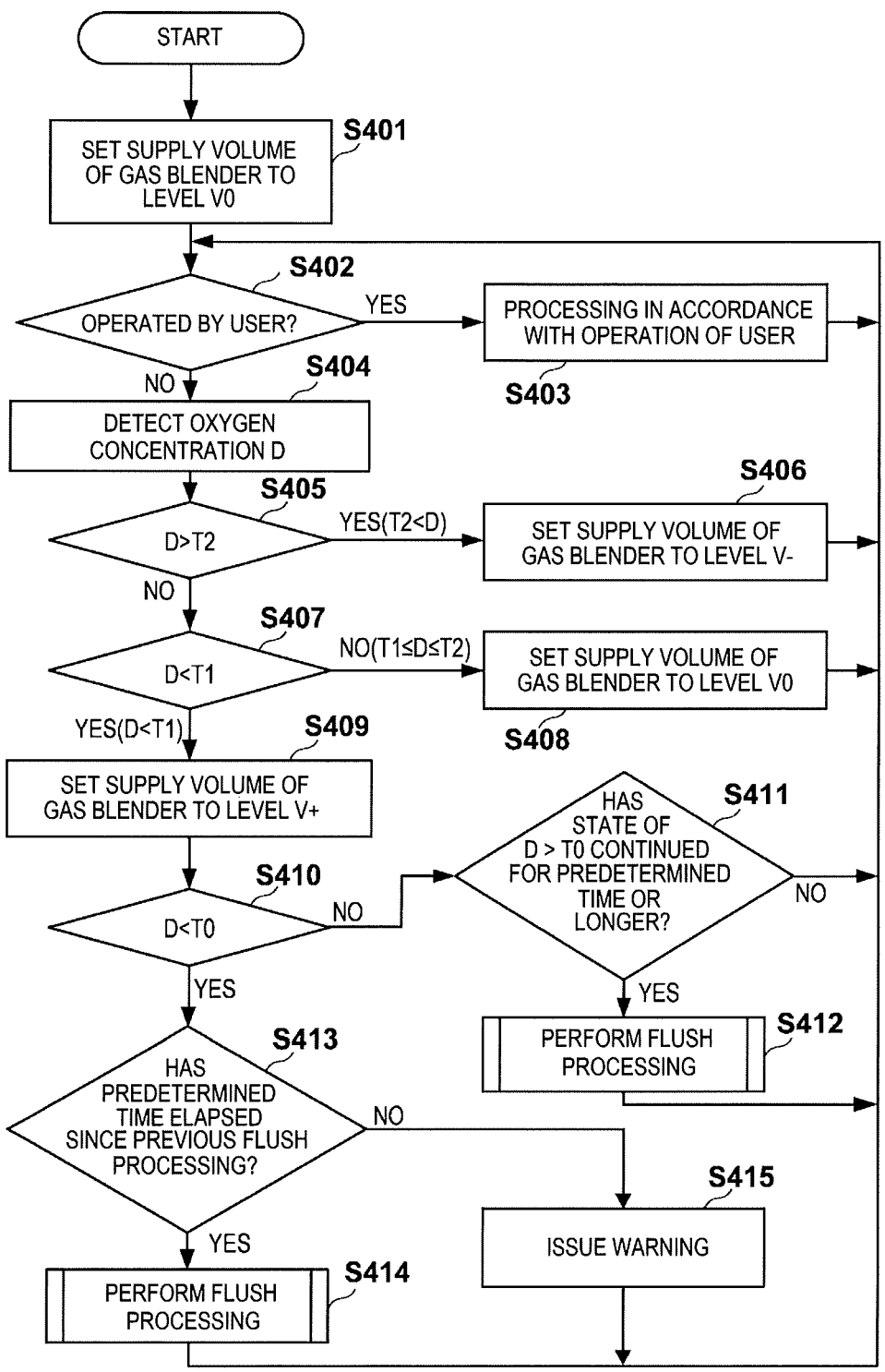
FIG. 4 is a flow chart illustrating a flow of control processing of the controller in the embodiment.

Taking the above descriptions into consideration, descriptions will be given in accordance with a flow chart in FIG. 4 regarding the contents of processing in the extracorporeal circulation operation mode of the controller 110 in the extracorporeal circulation apparatus 100 of the embodiment. FIG. 4 shows a portion inside the control program 210 in FIG. 2. Hereinafter, in order to make the description simple, descriptions will be focused on the processing based on oxygen concentration detected by a blood oxygen concentration sensor 125.

When the priming processing ends and the extracorporeal circulation operation mode starts, the control unit 201 first sets the gas supply volume of the gas blender 117 to the level "V0" in Step S401. In other words, in a state immediately before being in operation as the circulation circuit, the gas supply volume of the gas blender 117 is set to the level "Vmin". Therefore, processing to set the gas supply volume to the level "V0" is performed. As a result, the gas blender 117 starts to supply gas including oxygen to the artificial lung 113 at the set gas supply volume of the level V0.

Subsequently, the control unit 201 proceeds to Step S402 and determines whether or not a user operates the operation unit 202. If it is determined that there is an instructive input with respect to the operation unit 202 by a user, the procedure proceeds to Step S403, thereby performing processing in accordance with the instruction. The processing in Step S403 includes an operation of stopping the warning alarm, and the like.

When it is determined that there is no operation by a user, the procedure proceeds to Step S404, thereby detecting the blood oxygen concentration D by a blood oxygen concentration sensor 125. The detection is performed at the interval of 50 ms as described above. In addition, as described above, the average value of approximately ten latest results including the current detection value of a blood oxygen concentration sensor 125 is obtained as the current blood oxygen concentration D.

In Step S405, it is determined whether the obtained oxygen concentration D exceeds the threshold value T2. When it is determined to exceed thereof, it implies that gas exchange is performed more than necessary. Therefore, the procedure proceeds to Step S406, thereby setting the gas supply volume of the gas blender 117 to the level "V−".

Meanwhile, when it is determined that the oxygen concentration D is equal to or less than the threshold value T2, in Step S407, it is determined whether or not oxygen concentration falls below the threshold value T1. In a case of No, it implies that the oxygen concentration D is within the target range. Therefore, the procedure proceeds to Step S408, thereby setting the gas supply volume of the gas blender 117 to the level "V0". When the gas supply volume in the current setting is the same as the supply volume in the previous setting, it is not necessary to perform setting of the gas blender 117. It is similarly applied to the following descriptions.

Meanwhile, when it is determined that the oxygen concentration D falls below the threshold value T1, it is possible to determine that the gas exchange rate is dropping. Therefore, the procedure proceeds to Step S409, thereby setting the gas supply volume of the gas blender 117 to the level "V+".

Then, in Step S410, it is determined whether or not oxygen concentration falls below the threshold value T0. When it is determined to be No, the processing proceeds to Step S411, thereby determining whether or not the state of T0<D<T1 has continued for the time set in advance or longer. When there is no occurrence of a blood plasma leak in the artificial lung 113, the gas supply volume is set to the level V+, and then, oxygen concentration rises after a suitable time has elapsed. Therefore, it is determined to be No in Step S411.

The above-described processing is performed in a case where there is no occurrence of a blood plasma leak in the artificial lung 113 or the quantity of occurrence is small.

Figure 5:
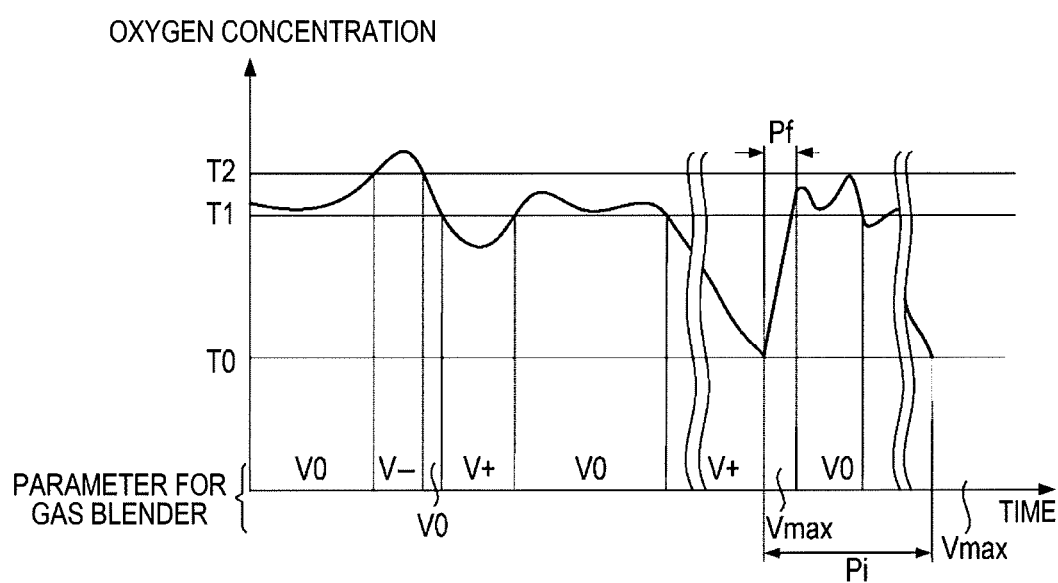
FIG. 5 is a diagram illustrating an example of transition of blood oxygen concentration in the embodiment.

FIG. 5 illustrates an example of transition of the blood oxygen concentration D. As illustrated therein, when the blood oxygen concentration D ranges from the threshold value T1 to T2, the gas supply volume is set to the level "V0". When D exceeds the threshold value T2, the gas supply volume is set to the level "V−". When D falls below the threshold value T1, the gas supply volume is set to the level "V+". As a result of performing the above-described processing, even though the blood oxygen concentration D of the artificial lung 113 on the downstream side may deviate a little from the target range of the threshold values T1 and T2, it is possible to exhibit the transition substantially within the range.

As the extracorporeal circulation circuit is constituted so as to be in an operation state, and several hours elapse, the gas exchange membrane of the artificial lung 113 starts to be covered with droplets of the blood plasma, thereby deteriorating the gas exchange rate. In this case, even though the gas supply volume is set to the level "V+", oxygen concentration cannot be raised, and the oxygen concentration D is maintained in a low state or keeps on dropping further. Finally, the oxygen concentration D falls below the threshold value T0. In the present embodiment, such circumstances are determined in Steps S410 and S411.

When the oxygen concentration D falls below the threshold value T0, in Step S413, it is determined whether or not a predetermined time period (three hours in the embodiment) has elapsed since the previous flush processing. When the operation starts as the extracorporeal circulation apparatus, the operation start time is acknowledged as the time of the previous flush processing. When it is determined that the predetermined time period has elapsed since the previous flush processing is performed, it is possible to presume that the oxygen concentration D falls below the threshold value T0 due to the blood plasma liquid which covers the gas exchange membrane of the artificial lung 113. Since the fall thereof is predicted, the flush processing is executed in Step S414. In Step S414, similar to the manually performed flush operation, the gas supply volume is continuously set to the level "Vmax" for approximately three minutes. A time period Pf in FIG. 5 is the time period in which the flush processing is performed.

Meanwhile, in Step S413, when it is determined that a time period Pi (refer to FIG. 5) since the previous flush processing is performed until the oxygen concentration D falling below the threshold value T0 is currently detected is less than a predetermined time period, it may be presumed that there is an occurrence of certain abnormality in the circulation circuit, particularly, in the artificial lung 113 and the periphery thereof. Therefore, the procedure proceeds from Step S413 to Step S415, thereby issuing a warning alarm.

Moreover, when a state of the oxygen concentration D in T0<D<T1 continues for the time set in advance or longer, it is strongly suspected that there is an occurrence of a blood plasma leak, thereby executing the flush processing in Step S412.

As described above, according to the extracorporeal circulation apparatus 100 of the present embodiment, the artificial lung in the circulation apparatus can be monitored and be maintained in a safe condition without manual assistance. In addition, even though the gas exchange rate is caused to be deteriorated due to the blood plasma liquid which covers the gas exchange membrane of the artificial lung, it is possible to automatically perform the flush processing. Thus, the artificial lung can be restored to the normal state. Moreover, according to the embodiment, when it is determined to perform the flush processing, if the elapsed time since the previous flush processing is shorter than the time interval set in advance, it is determined that there is an occurrence of certain abnormality, and a warning alarm can be issued. Thus, it is possible to urge a user to check the circulation circuit, particularly, the periphery of the artificial lung.

In the above-described embodiment, the gas blender 117 has been described to be controllable in five levels including the fully closed state of the valve. However, a gas blender which can be adjusted in more levels may be used. The present invention is not limited to the above-described embodiment.

In the above-described embodiment, the function is performed by a program executed by the control unit 201 inside the controller 110 which functions as the control device of the extracorporeal circulation apparatus 100. Therefore, it is clear that the program is included in the scope of the present invention. In addition, normally, the program is stored in a recording medium such as a CD-ROM, a memory card, or the like which can be read by a computer, and the program can be executed by being installed in the system. Therefore, it is clear that the recording medium is also included in the scope of the present invention.

The detailed description above describes a circulation apparatus and method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A circulation apparatus which causes blood of a patient to circulate outside a human body by using a circulation circuit, the apparatus comprising:
    a detector for detecting blood oxygen concentration after gas exchange performed in an artificial lung while being positioned on a downstream side of the artificial lung which is installed on the circulation circuit;
    a gas supply for supplying gas including at least oxygen to the artificial lung while having changeable supply volume per unit time; and
    a processor configured to execute flush processing by causing the gas supply to supply gas in volume sufficient to blow off a blood plasma liquid in a case where it is determined that the blood oxygen concentration detected by the detector falls within a predetermined range for a predetermined time or longer.

2. The circulation apparatus according to claim 1, wherein the processor is further configured to execute the flush processing in a case where it is determined that the blood oxygen concentration detected by the detector falls below the predetermined range.

3. A method of controlling a circulation apparatus which includes an artificial lung and a gas supply for supplying gas including at least oxygen to the artificial lung while having changeable supply volume per unit time and causes blood of a patient to circulate outside a human body using a circulation circuit, the method comprising:
    a detection step of detecting blood oxygen concentration after gas exchange performed in the artificial lung, based on a signal from a detector for detecting blood oxygen concentration positioned on a downstream side of the artificial lung which is installed on the circulation circuit; and
    a control step of executing flush processing by causing the gas supply to supply gas in volume sufficient to blow off a blood plasma liquid in a case where it is determined that the blood oxygen concentration detected in the detection step falls within a predetermined range for a predetermined time or longer.

4. The method of controlling a circulation apparatus according to claim 3, wherein the control step further executes the flush processing in a case where it is determined that the blood oxygen concentration detected in the detection step falls below the predetermined range.

5. A non-transitory, tangible computer readable recording medium storing a program which, when executed by a computer, causes the computer to control a circulation apparatus which includes an artificial lung and a gas supply for supplying gas including at least oxygen to the artificial lung while having changeable supply volume per unit time and causes blood of a patient to circulate outside a human body using a circulation circuit by performing the following steps:
    a detection step of detecting blood oxygen concentration after gas exchange performed in the artificial lung, based on a signal from a detector for detecting blood oxygen concentration positioned on a downstream side of the artificial lung which is installed on the circulation circuit; and
    a determination step of determining whether or not blood oxygen concentration detected by the detector falls below a threshold value; and
    a control step of executing flush processing by causing the gas supply to supply gas in volume sufficient to blow off a blood plasma liquid in a case where it is determined that the blood oxygen concentration detected in the detection step falls within a predetermined range for a predetermined time or longer.

6. The non-transitory, tangible computer readable recording medium according to claim 5, wherein the control step further executes the flush processing in a case where it is determined that the blood oxygen concentration detected in the detection step falls below the predetermined range.

* * * * *